United States Patent
Iida

(10) Patent No.: US 7,338,438 B2
(45) Date of Patent: Mar. 4, 2008

(54) SIGNAL OUTPUT APPARATUS OF ENDOSCOPE SYSTEM

(75) Inventor: Mitsuru Iida, Saitama (JP)

(73) Assignee: PENTAX Corporation, Tokyo (JP)

( * ) Notice: Subject to any disclaimer, the term of this patent is extended or adjusted under 35 U.S.C. 154(b) by 460 days.

(21) Appl. No.: 10/922,952

(22) Filed: Aug. 23, 2004

(65) Prior Publication Data

US 2005/0049456 A1 Mar. 3, 2005

(30) Foreign Application Priority Data

Aug. 29, 2003 (JP) ............... P2003-209531

(51) Int. Cl.
*A61B 1/045* (2006.01)
(52) U.S. Cl. ............... 600/109; 600/118; 348/74
(58) Field of Classification Search ............... 600/109, 600/118; 348/65, 74, 76; 345/636
See application file for complete search history.

(56) References Cited

U.S. PATENT DOCUMENTS

| 5,877,802 A | 3/1999 | Takahashi et al. |
|---|---|---|
| 5,902,230 A | 5/1999 | Takahashi et al. |
| 6,339,446 B1* | 1/2002 | Miyoshi ............... 348/65 |
| 6,677,983 B1* | 1/2004 | Takahashi et al. ......... 348/65 |
| 2001/0002842 A1 | 6/2001 | Ozawa et al. |
| 2001/0051762 A1* | 12/2001 | Murata et al. ............ 600/118 |
| 2002/0147384 A1* | 10/2002 | Uchikubo ............... 600/109 |
| 2003/0004398 A1* | 1/2003 | Takahashi ............... 600/109 |

OTHER PUBLICATIONS

U.S. Appl. No. 09/467,152, to Takahashi, filed Dec. 20, 1999.

* cited by examiner

*Primary Examiner*—John P. Leubecker
(74) *Attorney, Agent, or Firm*—Greenblum & Bernstein, P.L.C.

(57) ABSTRACT

An endoscope system comprises an electric scope, an input apparatus, a processing unit, and a computer. The electric scope has an imaging device. The input apparatus is used for inputting information of a patient. The processing unit outputs first electric signals which are obtained by the imaging device, and second electric signals which are obtained by the input apparatus, as image signals for peripheral devices. The computer is connected to the processing unit. The processing unit separately outputs first image signals corresponding to the first electric signals, and second image signals corresponding to the second electric signals, to the computer.

10 Claims, 9 Drawing Sheets

Fig. 3

SIGNAL OUTPUT APPARATUS OF ENDOSCOPE SYSTEM

BACKGROUND OF THE INVENTION

1. Field of the Invention

The present invention relates to an endoscope and in particular, relates to an image processing apparatus for transmitting image signals which are imaged by an imaging device of the endoscope and data signals input by an operation of a keyboard etc. to a computer.

2. Description of the Related Art

Endoscopes are used widely in the field of medicine, especially for the observation and inspection of the inside of an organ. Such endoscopes consist of an electric scope, an input apparatus, a color processing unit, and a TV monitor.

The electric scope has an imaging device such as a CCD, and images a subject. The imaging device is controlled by the color processing unit. The image signals obtained during the imaging process are converted to video signals corresponding to the connected peripheral apparatuses such as a TV monitor, by the color processing unit and are then output to the peripheral apparatuses. The TV monitor indicates images on the basis of video signals. An input apparatus, such as a keyboard, is used for inputting ID information of the patient such as a name etc. of a patient.

The video signals which are transmitted from the color processing unit to the TV monitor, for example, are analogue signals having analogue RGB component signals, Y/C separate signals, and NTSC (composite video) signals. Image signals, which are character signals and are input by the input apparatus, as the ID information of the patient, are overlapped with image signals of the photographic subjects which are analogue signals, by the OSD (On Screen Display) circuit etc. of the color processing unit. Accordingly, video signals which include the ID information are indicated on the TV monitor.

Imaging devices, which have comparatively few picture elements, are used for the electric scope in a conventional endoscope system. Therefore it has not been possible to obtain enough image information of the photographic subject to sufficiently use the total screen size of the TV monitor. Accordingly, when the image signals, which are character signals, are overlapped with the image signals of the photographic subject, a first indicating area for indicating the photographic subject and a second indicating area for indicating the ID information do not interfere with each other, so that the image of the photographic subject is indicated in the first indicating area which is a certain area of the TV monitor, and the image of the ID information is indicated in the second indicating area which is the remaining area or part of the remaining area of the TV monitor.

The left white area in FIG. 1 is the first indicating area and is for indicating the image of the photographic subject, and the right white area in FIG. 1 is the second indicating area and is for indicating the image of the ID information. FIG. 1 is an example of the TV monitor 50 which is described later and on which one image of the photographic subject, which is imaged by an electric scope with few picture elements, is indicated, in a conventional endoscope system. The full indicating area of the monitor is the shaded area around the circumference of the white areas, and inside the black areas.

In recent years, imaging devices which have a large number of picture elements have come to be used in electric scopes. In this case, the image corresponding to image signals of the photographic subject, which is imaged by the imaging device, is indicated on most of the indication area of the monitor, so that the image corresponding to image signals which are character signals, is indicated by overlapping on the image of the photographic subject.

In the middle part of the white area in FIG. 2, only an image of the photographic subject is indicated, however in the upper and lower parts of the white area in FIG. 2, the image of the ID information is indicated by being overlapped on the image of the photographic subject. FIG. 2 shows an example of the TV monitor 50 which is described later and on which one image of the photographic subject imaged by an electric scope which has many picture elements, is indicated, in a recent endoscope system. In the overlapping area, the image of the photographic subject is not seen.

In this recent endoscope system, an image of a photographic subject can be indicated as a large image on the monitor screen, so that there is the advantage that it becomes easier to observe the image of the photographic subject. However, the ID information is indicated by overlapping on the photographic subject, so that there is the disadvantage that the image of the ID information and the upper and lower ends of the image of the photographic subject become unclear.

Further, a processing unit which has the function of outputting digital image signals has been developed. In this case, a computer monitor which has a high density display, and which has comparatively high number of picture elements, is used as the monitor. The computer monitor is connected with the processing unit through a computer, so that it is possible to arrange the layout of the indicated image by using image filing software.

Regarding the software, the computer monitor can indicate a plurality of images of the photographic subject at one time, as in FIG. 3, in addition to indicating just one image of the photographic subject, as in FIG. 2.

Figure 3:
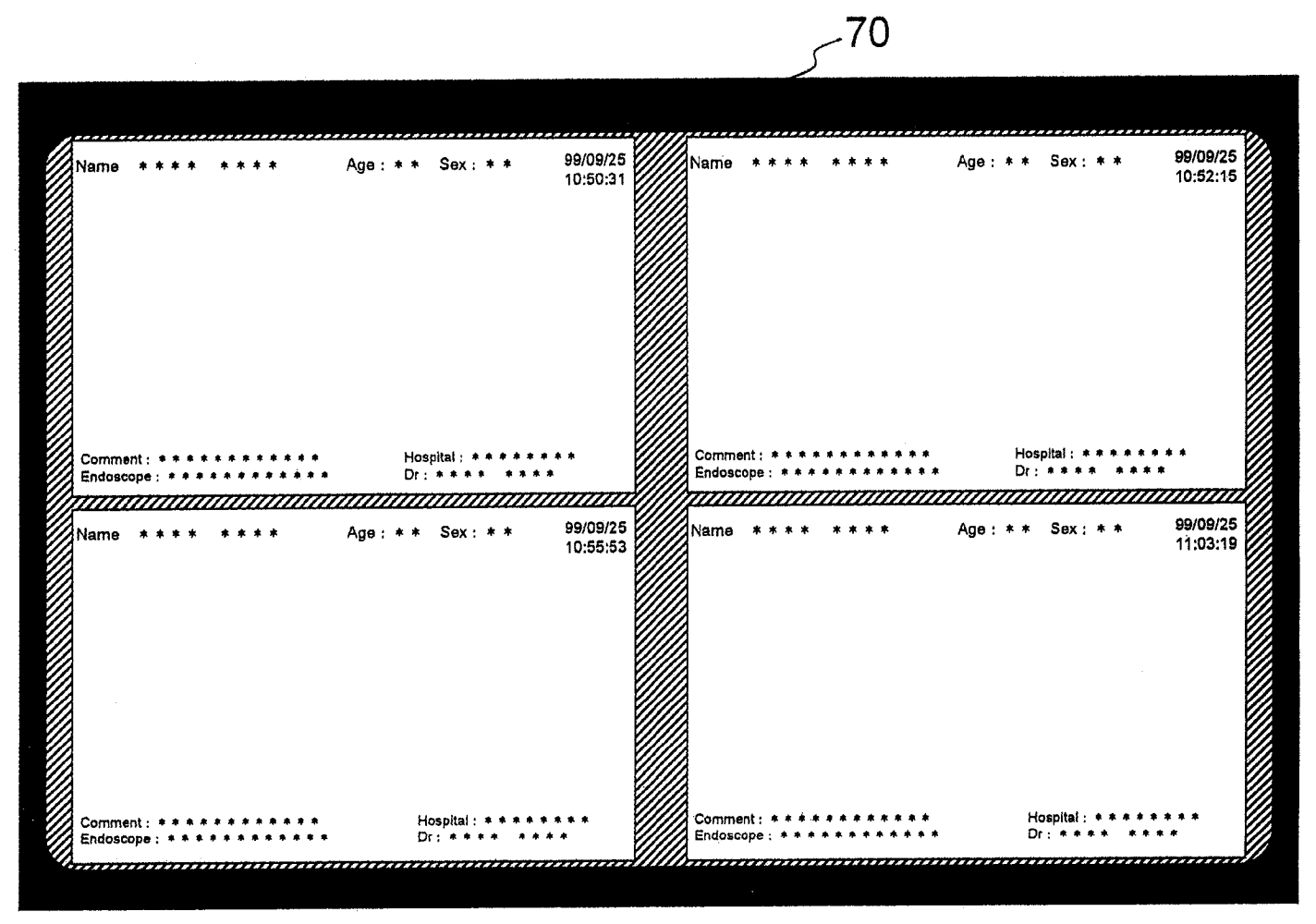

FIG. 3 shows an example where four images of a photographic subject, which was imaged by an electric scope having many picture elements, are indicated on the computer monitor 70, which is described later, of a recent endoscope system.

However, even if the image signals are output as digital signals, the image signals which are character signals corresponding to the ID information of the patient, are output under the condition where the character information is overlapped with the image of the photographic subject. Accordingly, the disadvantage of the unclear image of the ID information and the upper and lower ends of the image of the photographic subject, has not been overcome yet. Especially, when plural images of the photographic subject are indicated at the same time, it is very difficult to see because plural sets of ID information of the same patient are also indicated.

SUMMARY OF THE INVENTION

Therefore, an object of the present invention is to provide an apparatus that can separately output image signals corresponding to a photographic subject, which is imaged by an electric scope, and the image signals corresponding to the ID information of the patient, which are the character signals, to the computer.

According to the present invention, an endoscope system comprises an electric scope, an input apparatus, a processing unit, and a computer. The electric scope has an imaging device. The input apparatus is used for inputting information of a patient. The processing unit outputs first electric signals which are obtained by the imaging device, and second electric signals which are obtained by the input apparatus, as image signals for peripheral devices. The computer is connected to the processing unit.

The processing unit separately outputs first image signals corresponding to the first electric signals, and second image signals corresponding to the second electric signals to the computer.

BRIEF DESCRIPTION OF THE DRAWINGS

The objects and advantages of the present invention will be better understood from the following description, with reference to the accompanying drawings in which:

FIG. 3 is a figure which shows an example of a computer monitor where four images of a photographic subject, which was imaged by an electric scope having many picture elements, are indicated, in a recent endoscope system;

DESCRIPTION OF THE PREFERRED EMBODIMENTS

Figure 1:
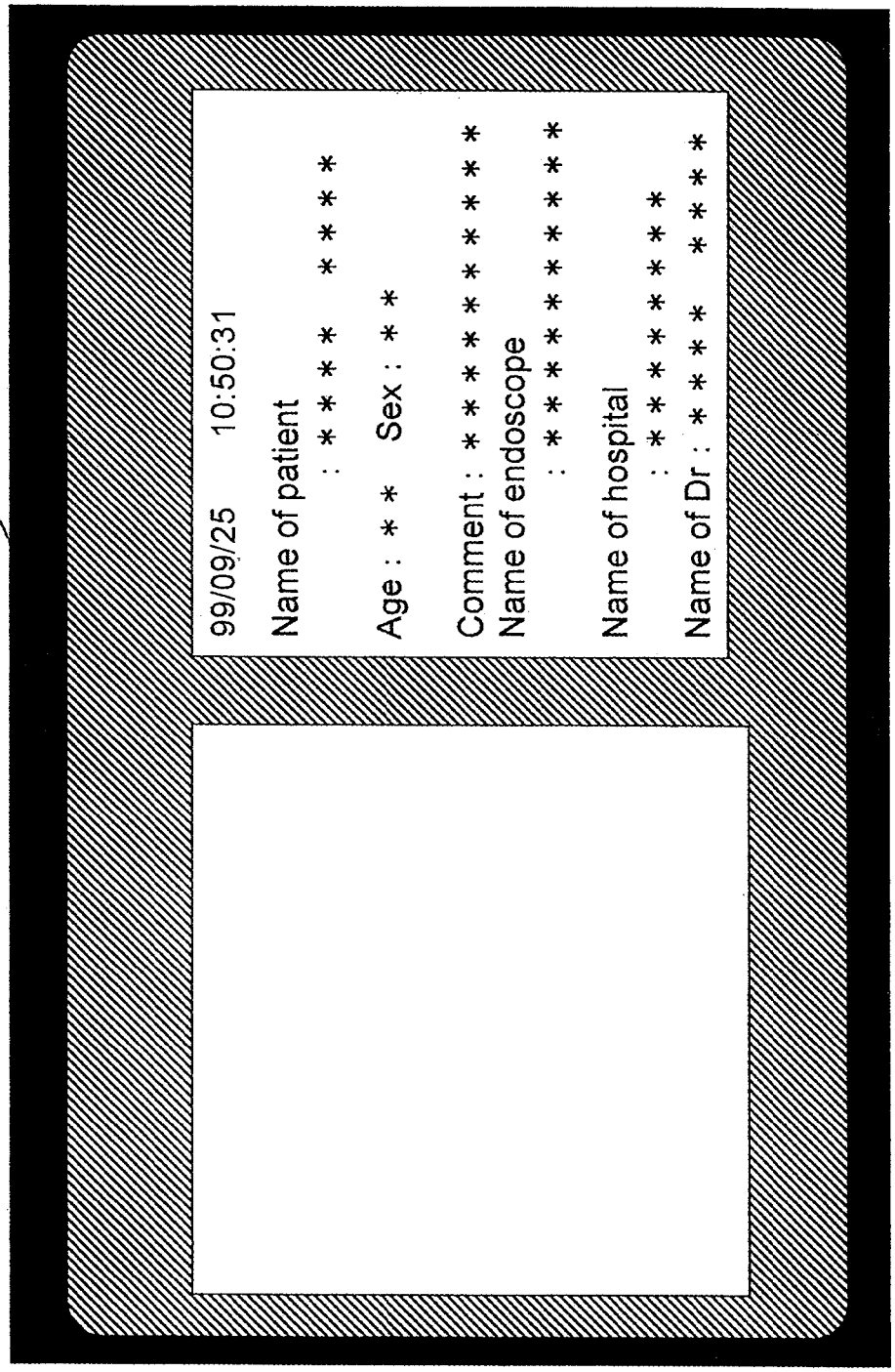
FIG. 1 is a figure which shows an example of a TV monitor where one image of a photographic subject, which was imaged by the electric scope having few picture elements, is indicated, in a conventional endoscope system.
Figure 2:
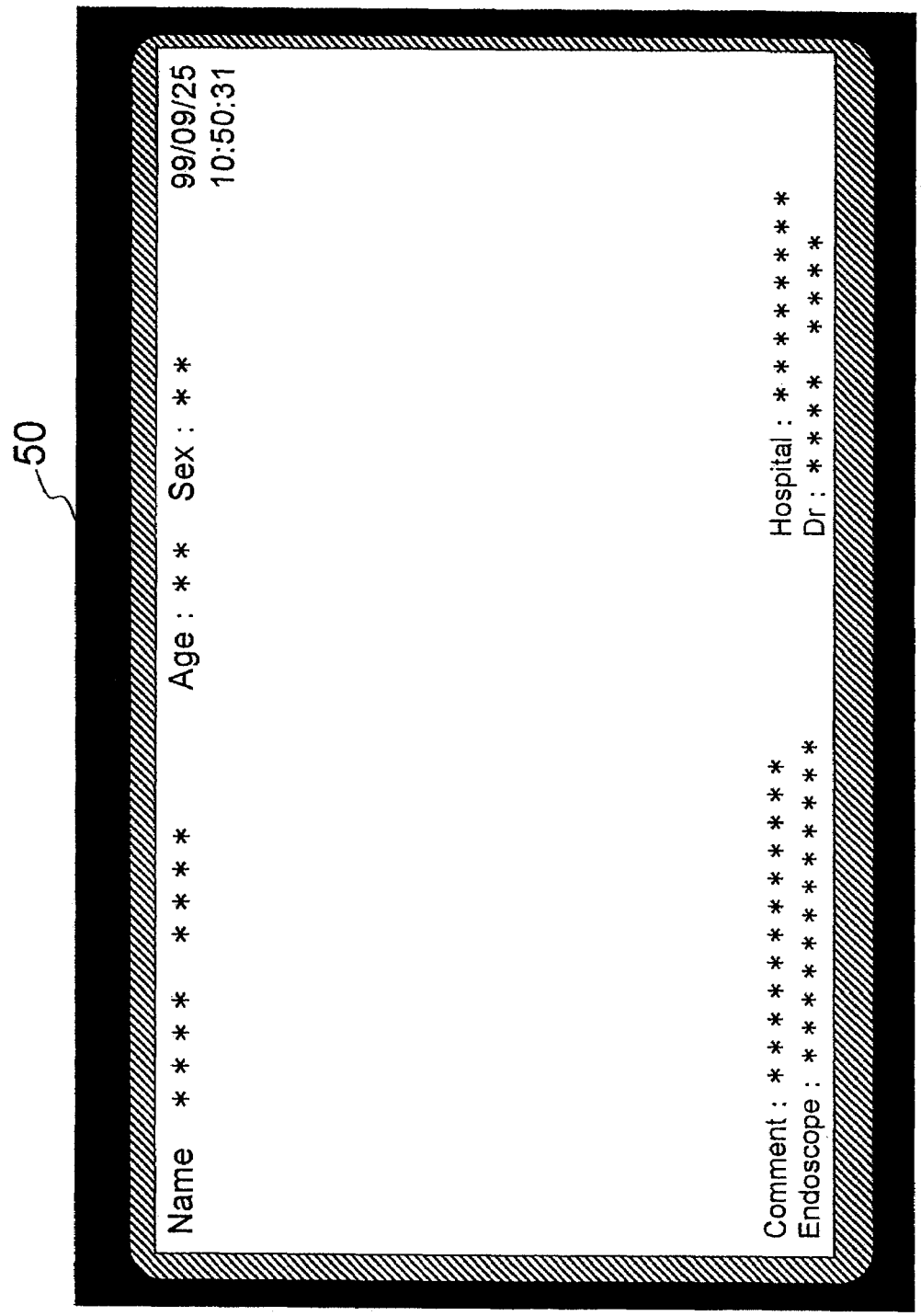
FIG. 2 is a figure which shows an example of a TV monitor where one image of a photographic subject, which was imaged by an electric scope having many picture elements, is indicated, in a recent endoscope system.
Figure 4:
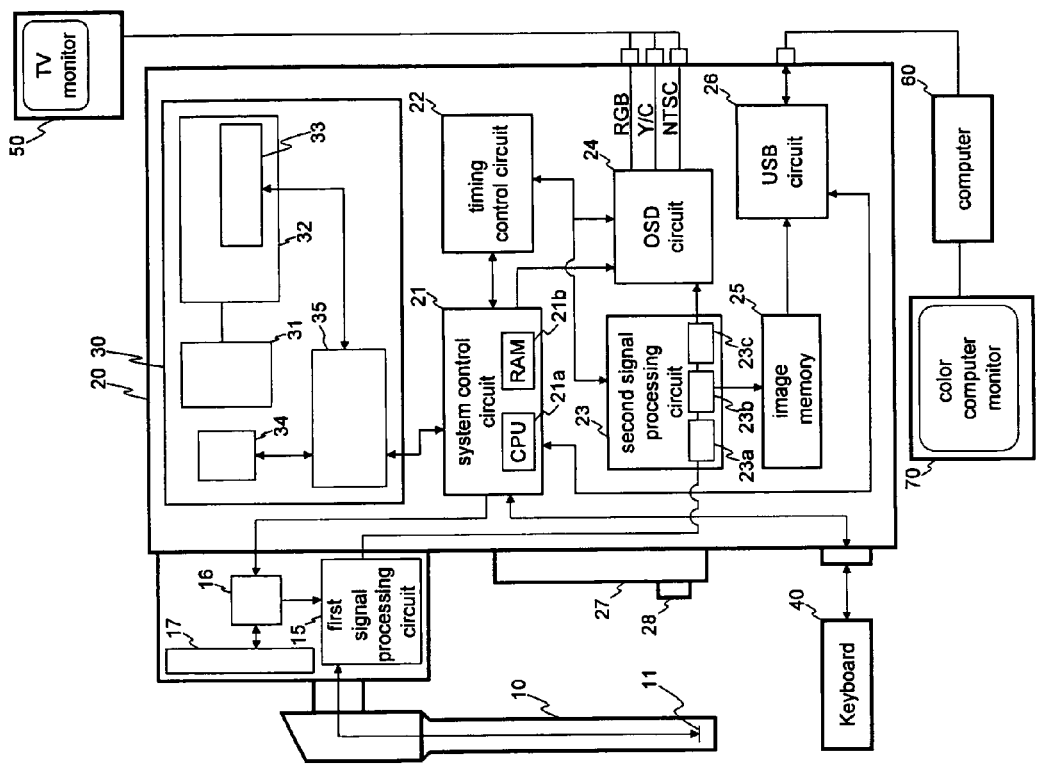
FIG. 4 is a block diagram of the endoscope system of this embodiment.

The present invention is described below with reference to the embodiments shown in the drawings. As shown in FIG. 4, an endoscope system relating to an embodiment of the present invention is provided with an electric scope 10, a color processing unit 20, a keyboard 40, a TV monitor 50 (or a video monitor), a computer 60 (or a personal computer), and a color computer monitor 70.

The electric scope 10 images a subject and is controlled by the color processing unit 20. The tip part of the electric scope 10 is inserted into an interior hollow of an organ where a photographic subject is imaged.

The color processing unit 20 outputs first image signals obtained by imaging the photographic subject, as video signals corresponding to the TV monitor 50, and as fourth image signals corresponding to the computer 60.

The keyboard 40 is operated by the operator, so that ID information such as the name of the patient is input.

The TV monitor 50 indicates the image of the photographic subject on the basis of the video signals.

The computer 60 stores still images of the photographic subject, and indicates the still images on the color computer monitor 70.

The electric scope 10 and the color processing unit 20 are detachably connected, the keyboard 40 and the color processing unit 20 are detachably connected, the color processing unit 20 and the TV monitor 50 are detachably connected, the color processing unit 20 and the computer 60 are detachably connected, and the computer 60 and the color computer monitor 70 are detachably connected.

The electric scope 10 has an imaging unit 11, and a lighting unit which is not depicted. The imaging unit 11 has an imaging device such as a CCD. The lighting unit supplies the appropriate light quantity from a light source unit 30 (which is described later) to the photographic subject. The imaging unit 11 images the illuminated photographic subject and then converts the image to first image signals.

The electric scope 10 has a first signal processing circuit 15, a microcomputer 16, and an EEPROM (Electrically Erasable Programmable Read-Only Memory) 17. The first signal processing circuit 15 has a CCD driver which drives the imaging device which is in the imaging unit 11. The first signal processing circuit 15 has a CDS (Correlated Double Sampling) circuit which reduces the noise components of the first image signals obtained by the imaging unit 11. These operations are carried out in accordance with clock pulse signals fed from a timing control circuit 22, by a system control circuit 21, through the microcomputer 16 and the EEPROM 17. The data regarding the characteristics of the electric scope 10 is stored in the EEPROM 17 in advance.

The color processing unit 20 has the system control circuit 21, the timing control circuit 22, a second signal processing circuit 23, and an OSD (On Screen Display) circuit 24.

The system control circuit 21 has a CPU 21a and a RAM 21b. The CPU 21a controls the operation etc. of the entire endoscope. The RAM 21b temporally stores the data signals for the operation of the entire endoscope. Especially, the input signals from the keyboard 40 such as character signals, are temporally stored in the RAM 21b as second image signals, by the CPU 21a.

The timing control circuit 22 outputs the clock pulse signals and synchronous signals, so that the timing control circuit 22 adjusts each process timing.

The second signal processing circuit 23 has an A/D (Analogue/Digital) converter 23a, an image-signal processing unit 23b, and a D/A (Digital/Analogue) converter 23c. The A/D converter 23a, the image-signal processing unit 23b, and the D/A converter 23c convert the first image signals obtained by the imaging unit 11 to third image signals corresponding to the OSD circuit 24. The A/D converter 23a and the image-signal processing unit 23b convert the first image signals to fourth image signals corresponding to a USB circuit 26 (which is described later).

The third image signals fed from the second signal processing circuit 23 are overlaid on the second image signals by the OSD circuit 24. The overlaid image signals are analogue video signals such as analogue RGB component signals. The video signals are supplied to the TV monitor 50 by the OSD circuit 24.

The color processing unit 20 has an image memory 25 and the USB (Universal Serial Bus) circuit 26. The image memory 25 temporally stores still images which are digital signals (the fourth image signals) and are converted from the first image signals corresponding to the computer 60 by the image-signal processing unit 23b, when the still images (the fourth image signals) are supplied to the computer 60. The USB circuit 26 is a digital signal transmission circuit which transmits digital signals (the fourth image signals that are temporally stored to the image memory 25 etc.) to the computer 60. The USB circuit 26 has a serial port for connecting to the computer 60.

The color processing unit 20 has a freeze switch 28 for obtaining still pictures on a front panel 27. Output signals (freeze signals) corresponding to the operation of the freeze switch 28 are input to the CPU 21a.

The color processing unit 20 has a light source 30. The light source 30 has a lamp 31, a lamp power supply 32, an iris 34, and a peripheral control unit 35, for transmitting light to the lighting unit in the tip part of the electric scope 10 through a light guidance system (an optical fiber bundling) which is not depicted. Controls of the light quantity of the lamp 31 and the iris 34 are carried out by the system control circuit 21 through the peripheral control unit 35.

The keyboard 40 is an input device for inputting ID information etc. of a patient. The operator inputs the ID information relating to the name of the patient corresponding to the image of the photographic subject, by using the keyboard 40.

Electric signals input by the operator through the keyboard 40 are transmitted to the OSD circuit 24 as the second image signals such as the character signals via the system control circuit 21. Electric signals input by the operator through the keyboard 40 are transmitted via the system control circuit 21 to the USB circuit 26 as the fifth image signals such as the character signals.

The TV monitor 50 is a typical monitor that is available in the market, and that can indicate images based on analogue video signals. The TV monitor 50 can indicate images based on video signals of the photographic subject, which are fed from the OSD circuit 24.

The computer 60 is a typical computer that is available in the market, and that can receive and process digital data. The digital image signals are transmitted to the computer 60 through the USB circuit 26.

The color computer monitor 70 is a typical high-resolution color monitor that is available in the market, and that can indicate signals which are processed by the computer 60. The color computer monitor 70 can indicate images based on digital image signals, which are the fourth and fifth image signals, in a proper manner.

Next, the operation of each component, in the endoscope system will be explained.

The photographic subject in the interior hollow of an organ, is imaged by the electric scope 10 under the control of the system control circuit 21. During imaging, the appropriate light quantity is supplied to the photographic subject by the light source unit 30.

The first image signals, which are imaged, are converted to third image signals corresponding to the OSD circuit 24 and the TV monitor 50, and to the fourth image signals corresponding to the USB circuit 26 and the computer 60, by the first and second signal processing circuits 15 and 23.

The character data etc. regarding the ID information, which is the name etc. of the patient, are input by the operator by using the keyboard 40, so that electric signals input by using the keyboard 40 are transmitted to the system control circuit 21. The second image signals corresponding to the electric signals input by using the keyboard 40 are temporally stored in the RAM 21b, and are transmitted to the OSD circuit 26 as character signals.

When video signals are indicated on the TV monitor 50, the third image signals, which are converted from digital to analogue by the D/A converter 23c, are transmitted to the OSD circuit 24. The electric signals input by using the keyboard 40 are converted to the second image signals, as the character signals, by the CPU 21a, and are then transmitted to the OSD circuit 24. The OSD circuit 24 overlays the second image signals on the third image signals. The overlaid image signals, which are analogue video signals such as the analogue RGB component signals, are transmitted to the TV monitor 50. The TV monitor 50 indicates the video images.

When the fourth image signals are transmitted to the computer 60, and are indicated on the color computer monitor 70, the fourth image signals are temporally stored in the image memory 25 without being converted from digital to analogue. The fourth image signals are still pictures. The timing of obtaining a still picture (the freeze timing) is decided when the freeze switch 28 is operated by the operator. The still picture signals (freeze signals) corresponding to the operation of the freeze switch 28 are input to the CPU 21a, so that the CPU 21a controls each component corresponding to the still picture signals. The still images represent a smaller quantity of data to transmit to the computer 60 and require less processing time in the computer 60, in comparison with the motion pictures.

Next, the fourth image signals corresponding to the first image signals of the photographic subjects and the fifth image signals corresponding to the electric signals input by using the keyboard 40, are transmitted to the computer 60. The fourth image signals which are temporally stored in the image memory 25 and which are signals relating to the photographic subject, are transmitted to the USB circuit 26 without overlaying of the fifth image signals. The fifth image signals which are temporally stored in the RAM 21b, and which are signals relating to the character information, are transmitted to the USB circuit 26. The USB circuit 26 separately transmits the fourth and fifth image signals in digital format to the computer 60. The transmitted fourth and fifth image signals are arranged in a proper layout by the image-processing software etc. installed in the computer 60. The color computer monitor 70 indicates the fourth and fifth image signals which are arranged in the proper layout. The fifth image signals are composed of ASCII code which can be converted to specified character information etc. It is easy for the computer 60 to convert the fifth image signals to character information etc. which can be indicated on the color computer monitor 70.

The arrangement of the proper layout is carried out by exclusive image-filing software which is installed in the computer 60. The exclusive image-filing software is set up so that the first area which indicates the photographic image and the second area which indicates the character information etc. have a proper location relation on the screen.

Figure 5:
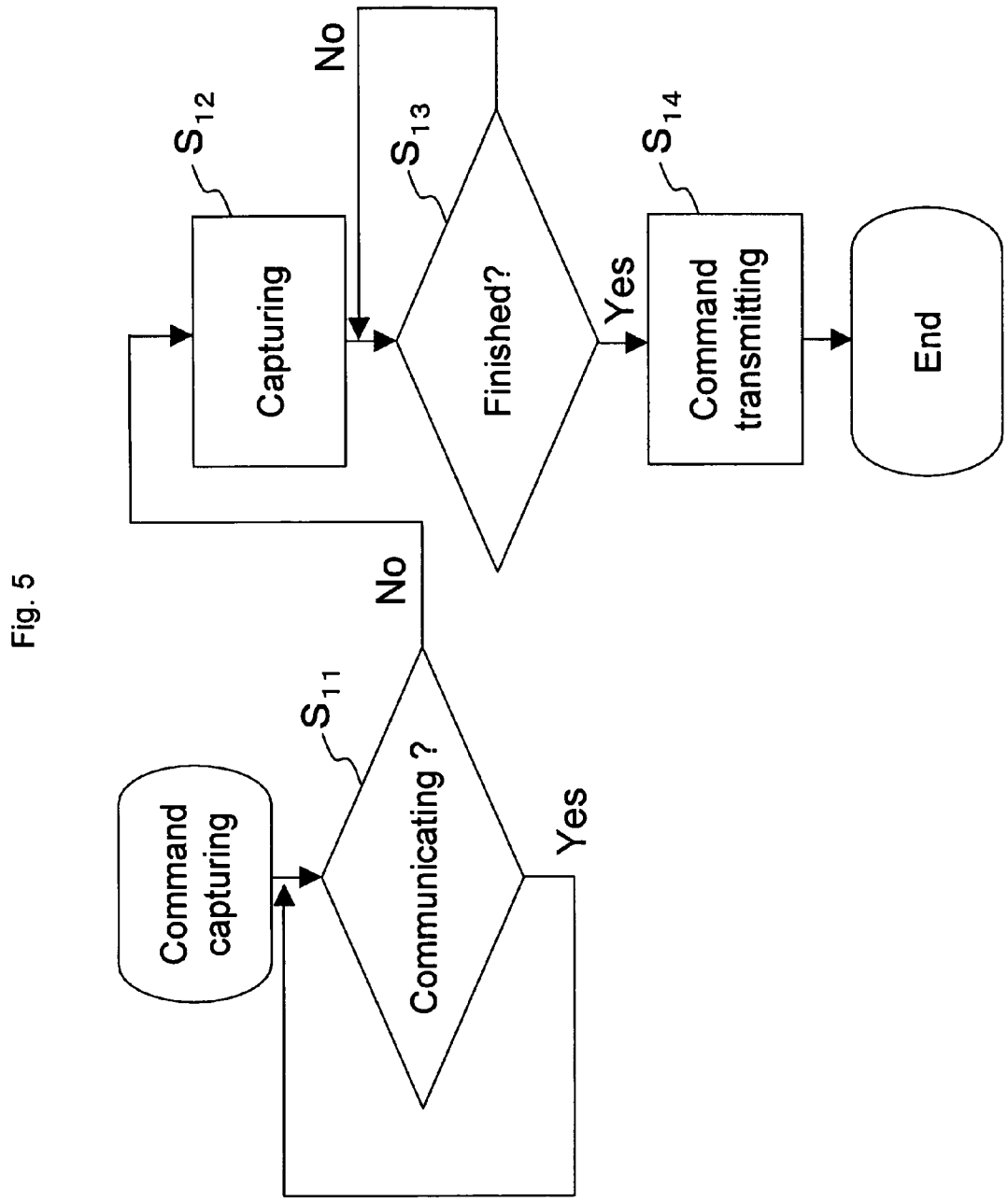
FIG. 5 is a flowchart of a first processing flow of fourth image signals by the CPU.
Figure 6:
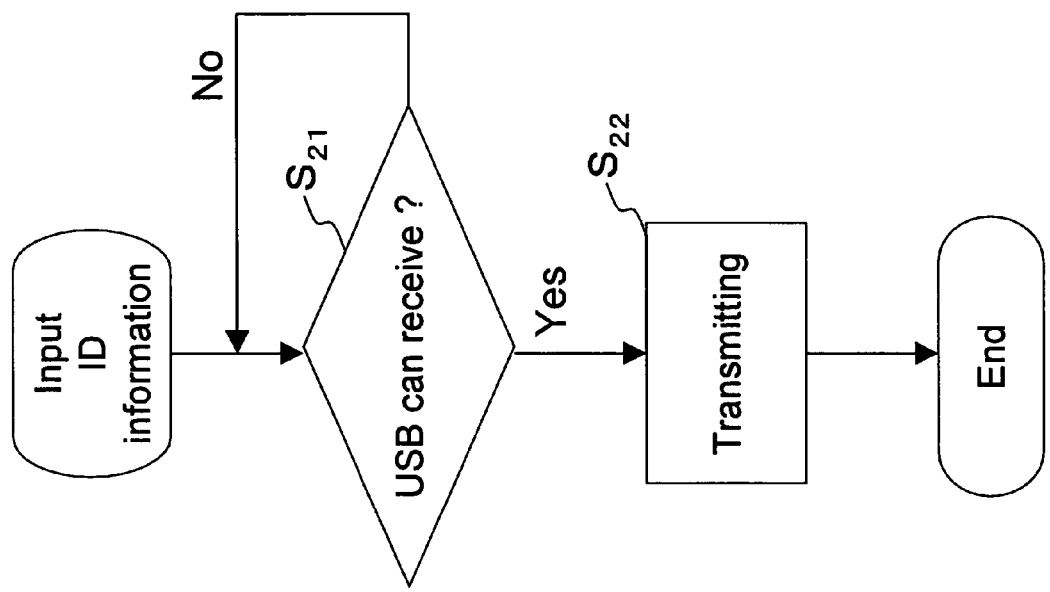
FIG. 6 is a flowchart of a second processing flow of fifth image signals by the CPU.
Figure 7:
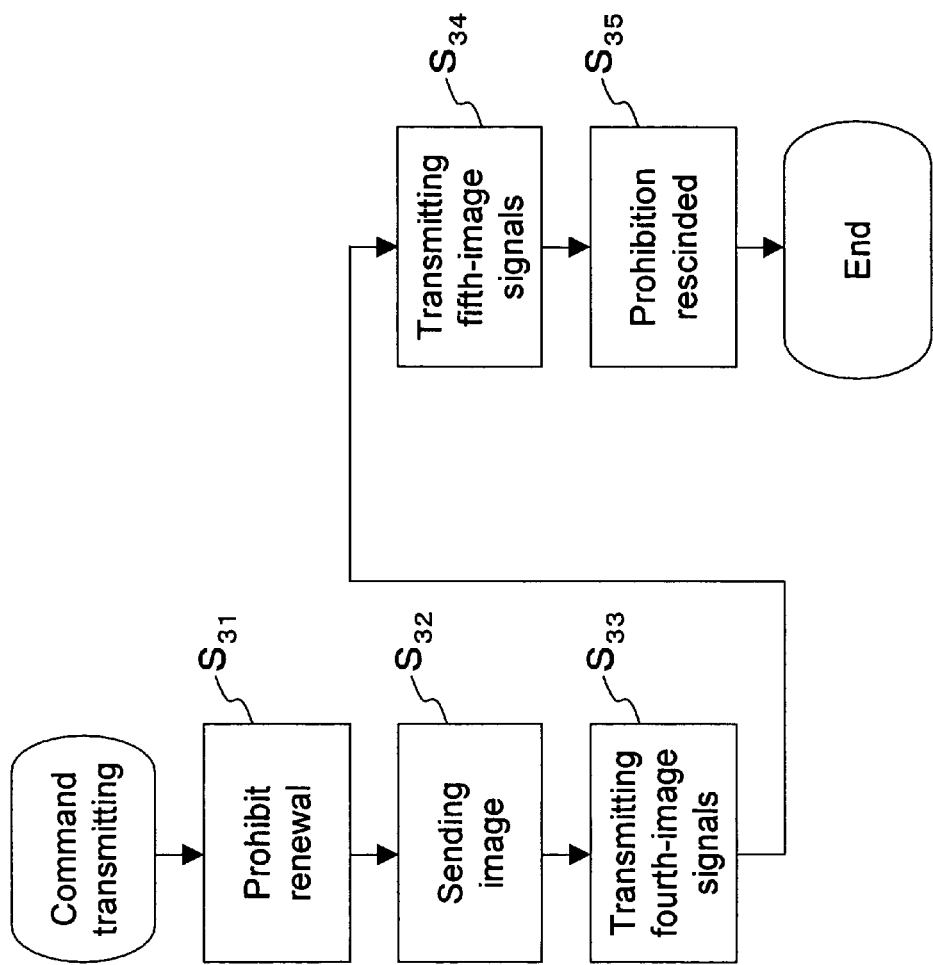
FIG. 7 is a flowchart of a third processing flow of fourth and fifth image signals by the USB circuit.

In FIG. 5~FIG. 7, flow charts explain how the fourth image signals corresponding to the first image signals of the photographic subject are transmitted to the computer 60, and how the fifth image signals corresponding to the electric signals input by the keyboard 40 are transmitted to the computer 60. FIG. 5 shows a first processing flow of the fourth image signals by the CPU 21a. FIG. 6 shows a second processing flow of the fifth image signals by the CPU 21a. FIG. 7 shows a third processing flow of the fourth and fifth image signals by the USB circuit 26.

When the still picture signals corresponding to the operation of the freeze switch 28 by the operator, are input to the CPU 21a, the CPU 21a controls each component corresponding to the still picture signals, for the capture command. In step $S_{11}$ in FIG. 5, it is judged whether or not the USB circuit 26 and the computer 60 are communicating.

When it is judged that they are not communicating, the fourth image signals are captured and stored in the image memory 25 in step $S_{12}$. In step $S_{13}$, it is confirmed that the capturing is finished. Then, the command for the fourth image signals which were captured and stored in the image memory 25 to be output to the computer 60, is sent to the USB circuit 26 in step $S_{14}$. When it is judged in step $S_{11}$ that the USB circuit 26 and the computer 60 are communicating, the fourth image signals are not captured and are not stored in the image memory 25.

When the ID information such as the name of the patient is input by operating the keyboard 40, the fifth image signals corresponding to the electric signals input by using the keyboard 40 are temporally stored in the RAM 21b by the CPU 21a. In step $S_{21}$ in FIG. 6, it is judged whether or not the USB circuit 26 can receive the fifth image signals. When the USB circuit 26 can receive the fifth image signals, the fifth image signals which are temporally stored in the RAM 21b are transmitted to the USB circuit 26.

When the still picture signals are input to the CPU 21a, the fourth image signals are captured and stored in the image memory 25, and the command from the CPU 21a, to output the fourth image signals to the computer 60, is sent to the USB circuit 26 (see FIG. 5). In step $S_{31}$ in FIG. 7, the condition where the USB circuit 26 and the computer 60 are communicating, is set by the USB circuit 26, so that during this time, the renewal of the image memory 25 is prohibited. In step $S_{32}$, the fourth image signals are sent to the USB circuit 26 from the image memory 25. The fourth image signals are transmitted to the computer 60 in step $S_{33}$. The fifth image signals corresponding to the electric signals input by using the keyboard 40, which are temporally stored in the RAM 21b, are transmitted to the USB circuit 26, so that the fifth image signals are transmitted to the computer 60 in step $S_{34}$. After transmitting the fourth and fifth image signals, the condition where the USB circuit 26 and the computer 60 are not communicating, is set by the USB circuit 26, so that the prohibition condition of the renewal of the image memory 25 is rescinded in step $S_{35}$.

Figure 8:
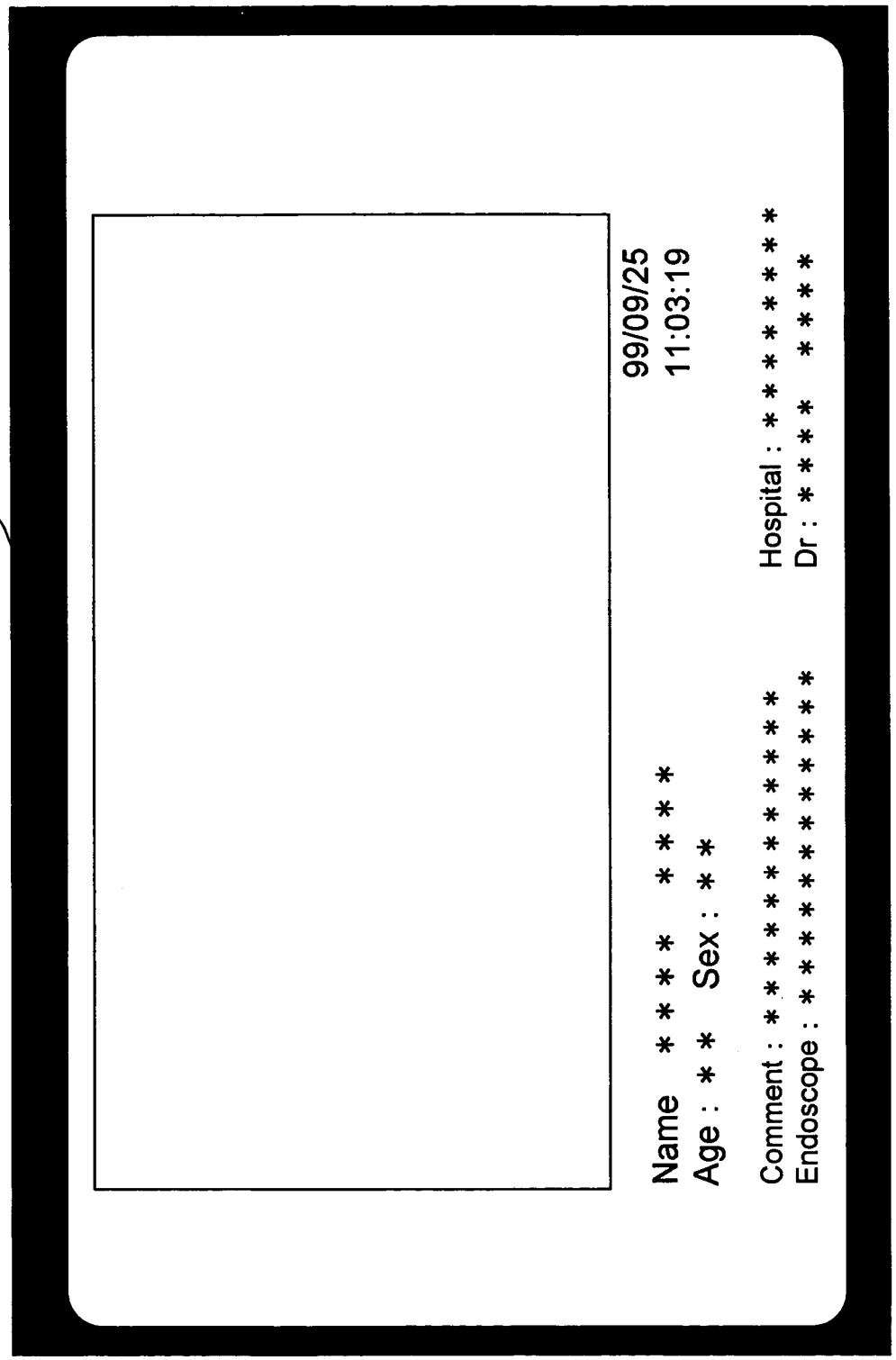
FIG. 8 is a figure which shows an example where one image of a photographic subject, which is imaged by an electric scope having many picture elements, is indicated on the computer monitor, in this embodiment.

It is possible to separately transmit the fourth image signals corresponding to the first image signals of the photographic subjects and the fifth image signals corresponding to the electric signals input by using the keyboard 40, to the computer 60, by these processes. It is also possible to clearly observe the imaging results where the indicating area of the fourth image signals and the indicating area of the fifth image signals are separated, by properly arranging the layout with image-processing software etc (see FIG. 8).

Figure 9:
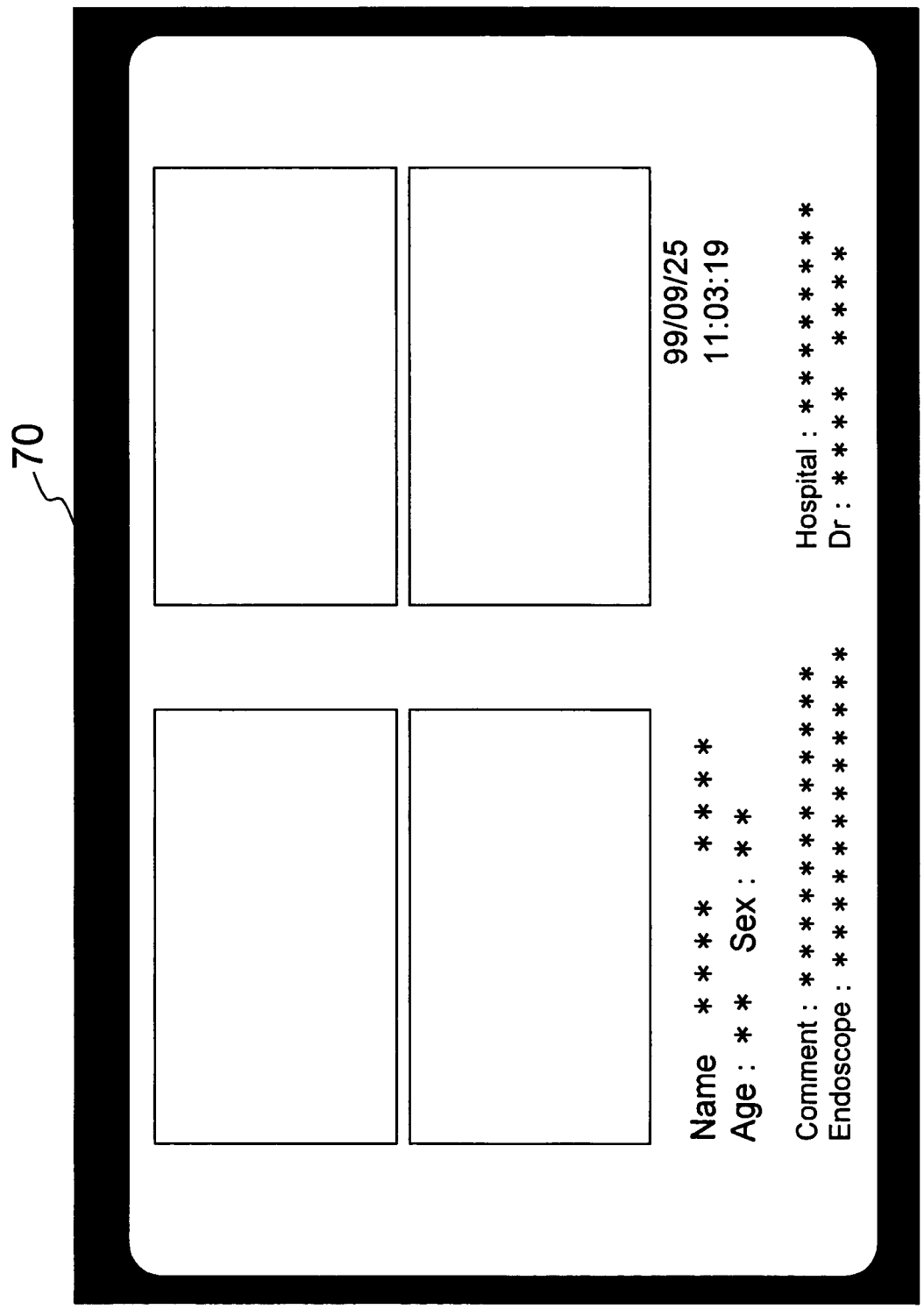
FIG. 9 is a figure which shows an example where four images of a photographic subject which is imaged by an electric scope having many picture elements, are indicated on the computer monitor, in this embodiment.

Further, the image-processing software can control the computer 60 to indicate a plurality of photographic subject images from the same patient, on one the screen of the color computer monitor 70 (see FIG. 9). In this case, it is possible to indicate only one ID information of the patient from the fifth image signals and photographic subject images from the fourth image signals on different areas of a screen of the color computer monitor 70.

Transmitting the fourth and fifth image signals separately in a single capturing operation of a still image is useful because the problem of not being able to see the ID information (the fifth image signals) of the patient due to the image signal (the fourth image signals) of the photographic subject, does not occur.

In this embodiment, the fourth and fifth image signals are digital signals, however they may be analogue signals similar to the signals which are transmitted to the TV monitor 50 from the color processing unit 20. In this case, the computer 60 has a video capturing function, so that the computer 60 captures still images on the basis of video-signals corresponding to the first image signals of the photographic subjects, and captures images on the basis of video-signals corresponding to the electric signals input by using the keyboard 40, and then carries out the indication control of these video-signals.

Whether the fourth and fifth image signals are transmitted to the computer 60 from the color processing unit 20 as a plurality of file information or as one single file is not important. The effect of the present invention is obtained if the fourth and fifth image signals are separately transmitted to the computer 60 in a single operation, and is not related to the file form. The fourth and fifth image signals can be in the bitmap (BMP) file form, the Joint Photographic Expert Group (JPEG) file form, or other various file forms.

In this embodiment, the fifth image signals corresponding to the electric signals input by using the keyboard 40 are the signals corresponding to character information, and are composed of ASCII code, however the fifth image signals may be in a different format and may be composed of image information in addition to character information. The reason for this is that it is possible to arrange a proper indicating layout after transmitting the fourth and fifth image signals.

The USB circuit 26 may be a digital signal transmission circuit which has another serial port accessible to the computer 60.

In this embodiment, capturing the still picture is carried out by the operation of the freeze switch 28, however capturing the still picture may be carried out by other means. For example, the computer 60 has a control function of the color processing unit 20, so that the freeze timing is decided by a command operation, by the operator of the input apparatus for the computer, which can be a mouse etc. and is not depicted.

The input means of the ID information of the patient etc. is not limited to keyboard input. Instead of by keyboard 40, ID information of the patient etc. may be input by using the touch panel control input on a TV monitor 50, the GUI (Graphical User Interface) on the color computer monitor 70, and speech recognition means which is installed in the computer 60.

Although the embodiments of the present invention have been described herein with reference to the accompanying drawings, obviously many modifications and changes may be made by those skilled in this art without departing from the scope of the invention.

The present disclosure relates to subject matter contained in Japanese Patent Application No. 2003-209531 (filed on Aug. 29, 2003) which is expressly incorporated herein by reference, in its entirety.

The invention claimed is:

1. An endoscope system comprising:
    an electric scope which has an imaging device;
    an input apparatus which is used for inputting information of a patient;
    a processing unit which outputs first electric signals which are obtained by said imaging device, and second electric signals which are obtained by said input apparatus, as image signals for peripheral devices; and
    a computer which is connected to said processing unit;
    said processing unit separately outputting first image signals corresponding to said first electric signals, and second image signals corresponding to said second electric signals to said computer.

2. The endoscope system according to claim 1, wherein said first and second image signals are digital signals;

said processing unit has an image memory which temporally stores said first image signals, a RAM which temporally stores said second image signals, and a digital signal transmission circuit which transmits said temporally stored first image signals and said temporally stored second image signals, to said computer.

3. The endoscope system according to claim 2, wherein said image memory temporally stores signals corresponding to still images of photographic subjects imaged by said imaging device, as said first image signals.

4. The endoscope system according to claim 3, further comprising a freeze switch which is operated in order to decide the timing for temporally storing said still images.

5. The endoscope system according to claim 2, wherein said second image signals are composed of signals for indicating character information.

6. The endoscope system according to claim 5, wherein said signals for indicating character information are composed of ASCII code.

7. The endoscope system according to claim 1, wherein the outputting of said first and second image signals is carried out in a single capturing operation of a still image.

8. The endoscope system according to claim 1, further comprising a computer monitor which indicates images on the basis of said first and second image signals output by said computer.

9. An endoscope system comprising:
an electric scope which has an imaging device;
an input apparatus which is used for inputting character information;
a processing unit which outputs first electric signals which are obtained by said imaging device, and second electric signals which are obtained by said input apparatus, as image signals for peripheral devices; and
a computer which is connected to said processing unit;
said processing unit separately outputting first image signals corresponding to said first electric signals, and second image signals corresponding to said second electric signals to said computer.

10. A processing unit for an endoscope system which outputs first electric signals which are obtained by an imaging device, and second electric signals which are obtained by an input apparatus which is used for inputting character information, as image signals for peripheral devices,
wherein said processing unit separately outputting first image signals corresponding to said first electric signals, and second image signals corresponding to said second electric signals to a computer which connects to said processing unit.

* * * * *